United States Patent [19]
Hayashi et al.

[11] Patent Number: 5,621,129
[45] Date of Patent: Apr. 15, 1997

[54] OPTICALLY ACTIVE TERTIARY PHOSPHINE COMPOUND, TRANSITION METAL COMPLEX COMPRISING THE SAME AS LIGAND AND PROCESS FOR PREPARING OPTICALLY ACTIVE ORGANIC SILICON COMPOUND USING SAID TRANSITION METAL COMPLEX

[75] Inventors: Tamio Hayashi; Masayoshi Minai, both of Shiga; Kazunori Iwakura, Osaka, all of Japan

[73] Assignee: Sumitomo Chemical Co., Ltd., Osaka, Japan

[21] Appl. No.: 612,108

[22] Filed: Mar. 7, 1996

[30] Foreign Application Priority Data

| | | | |
|---|---|---|---|
| Mar. 9, 1995 | [JP] | Japan | 7-049685 |
| Mar. 10, 1995 | [JP] | Japan | 7-051094 |
| Mar. 10, 1995 | [JP] | Japan | 7-051482 |
| Sep. 18, 1995 | [JP] | Japan | 7-238204 |

[51] Int. Cl.$^6$ ............................ C07F 9/02; C07F 15/00
[52] U.S. Cl. .................. 556/21; 556/23; 556/136; 556/138; 556/479; 568/17
[58] Field of Search ................... 556/21, 23, 136, 556/138, 479; 568/17

[56] References Cited

FOREIGN PATENT DOCUMENTS 0503884  9/1992  European Pat. Off. .

OTHER PUBLICATIONS

Uozumi et al., *Tetrahedron*, vol. 50, No. 15, pp. 4293–4302, 1994.
Hayashi et al., *J. Am. Chem. Soc.*, vol. 117, No. 35, pp. 9101–9102, 1995.
Uozumi et al., *Tetrahedron: Asymmetry*, vol. 4, No. 12, pp. 2419–2422, 1993.
Hayashi et al., *Tetrahedron Letters*, vol. 21, pp. 1871–1874, 1980.
Kurz et al., *Tetrahedron Letters*, vol. 31, No. 44, pp. 6321–6324, 1990.
Hattori et al., *Synthesis*, pp. 199–202, 1994.

*Primary Examiner*—Porfirio Nazario-Gonzalez
*Attorney, Agent, or Firm*—Birch, Stewart, Kolasch & Birch, LLP

[57] ABSTRACT

A tertiary phosphine compound of the formula (1):

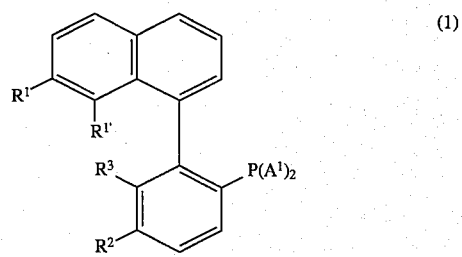

(1)

in which $R^1$ and $R^{1'}$ are hydrogen atoms or together form —CH=CH—CH=CH—; $R^2$ and $R^3$ together form a group of the formula (a):

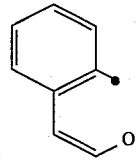

in which —● represent a bond to be bonded to the $R^3$ group, and —o represents a bond to be bonded to the $R^2$ group when $R^1$ and $R^{1'}$ together form —CH=CH—CH=CH—, or when $R^1$ is a hydrogen atom, $R^2$ and $R^3$ together form —CH=CH—CH=CH— or $R^2$ is a hydrogen atom and $R^3$ is a substituted or unsubstituted alkyl group, or a substituted or unsubstituted phenyl group; $A^1$ is a 3-trifluoromethylphenyl group or a 3,5-bis(trifluoromethyl)phenyl group when $R^1$ is a hydrogen atom and $R^2$ and $R^3$ together form —CH=CH—CH=CH—, or a substituted or unsubstituted phenyl group when $R^1$ is not a hydrogen atom or when $R^2$ and $R^3$ do not together form —CH=CH—CH=CH—.

5 Claims, No Drawings

OPTICALLY ACTIVE TERTIARY PHOSPHINE COMPOUND, TRANSITION METAL COMPLEX COMPRISING THE SAME AS LIGAND AND PROCESS FOR PREPARING OPTICALLY ACTIVE ORGANIC SILICON COMPOUND USING SAID TRANSITION METAL COMPLEX

BACKGROUND OF THE INVENTION

1. Field of the Invention

The present invention relates to a tertiary phosphine compound which is coordinated to transition metals to form catalysts useful in various asymmetric synthesis reactions, a transition metal complex comprising said phosphine compound as a ligand, and a process for preparing an optically active organic silicon compound using said transition metal complex as a catalyst.

2. Description of the Belated Art

Hitherto, many reports have been made on transition metal catalysts used in the asymmetric synthesis reactions. It is well known that, among these catalysts, complexes of transition metals such as ruthenium, palladium and rhodium which comprise an optically active tertiary phosphine compound as a ligand have the excellent catalytic activities in the asymmetric syntheses (see JAPAN CHEMICAL SOCIETY Ed., ELEMENTS OF CHEMISTRY ("KAGAKU SOSETSU") 32, "Chemistry of Organic Metal Complexes" (1982) 237–238).

Japanese Patent KOKAI Publication No. 6193/1980 discloses a rhodium complex comprising 2,2-bis(diphenylphosphino)-1,1'-binaphthyl having an axial asymmetry as a ligand.

But, it is also known that a selectivity and a yield of the reaction product vary greatly depending on the kinds of the transition metal complexes, types of the reactions in which the metal complexes are used, kinds of reactants, and so on.

Optically active organic silicon compounds are useful compounds which are used as intermediates in the production of optically active compounds such as medicines, agrochemicals, and ferroelectric liquid crystals, since they can be easily converted to optically active alcohols or halogen compounds by replacing a silyl group with a corresponding functional group.

Hitherto, the optically active organic silicon compound are prepared by an asymmetric hydrosilylation reaction of an olefin. As an asymmetric hydrosilylation reaction of a styrene derivative, Tetrahedron Lett., 21, 1871 (1980) and Tetrahedron Asymmetry, 4, 2419 (1993) disclose a process using palladium-[2-(diphenylphosphino)-1,1'-biphenyl] complex. However, an optical yield of the desired product is low, and a catalytic property of the complex is still unsatisfactory.

SUMMARY OF THE INVENTION

An object of the present invention is to provide a novel tertiary phosphine compound which can unexpectedly improve catalytic activities such as stereoselectivity or regioselectivity in comparison with the conventional catalysts, in asymmetric hydrosilylation reactions of various styrene derivatives.

Another object of the present invention is to provide a transition metal complex comprising such tertiary phosphine compound as a ligand.

A further object of the present-invention is to provide a process for preparing an optically active organic silicon compound using said transition metal complex as a catalyst.

According to a first aspect of the present invention, there is provided a tertiary phosphine compound of the formula (1):

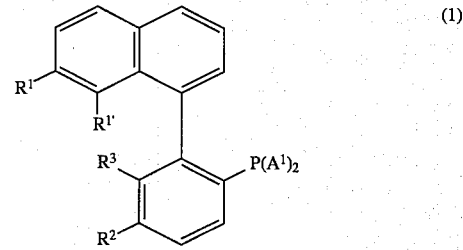

wherein $R^1$ and $R^{1'}$ are hydrogen atoms or together form a group of the formula: —CH=CH—CH=CH—; $R^2$ and $R^3$ together form a group of the formula (a):

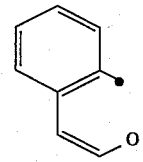

in which —● represent a bond to be bonded to the $R^3$ group, and —o represents a bond to be bonded to the $R^2$ group when $R^1$ and $R^{1'}$ together form a group of the formula: —CH=CH—CH=CH—, or when $R^1$ is a hydrogen atom, $R^2$ and $R^3$ together form a group of the formula: —CH=CH—CH=CH— or $R^2$ is a hydrogen atom and $R^3$ is an alkyl group which may be substituted by a halogen atom, a lower alkoxy group or a halogenated lower alkyl group, or a phenyl group which may be substituted by a halogen atom, a lower alkyl group or a halogenated lower alkyl group; $A^1$ is a 3-trifluoromethylphenyl group or a 3,5-bis(trifluoromethyl)phenyl group when $R^1$ is a hydrogen atom and $R^2$ and $R^3$ together form a group of the formula: —CH=CH—CH—CH—, or a phenyl group which may be substituted by a halogen atom, a lower alkyl group, a lower alkoxy group or a halogenated lower alkyl group when $R^1$ is not a hydrogen atom or when $R^2$ and $R^3$ do not together form a group of the formula: —CH=CH—CH=CH—.

According to a second aspect of the present invention, there is provided a transition metal complex comprising said tertiary phosphine compound (1) as a ligand.

According to a third-aspect of the present invention, there is provided a process for producing an optically active organic silane compound of the formula (2):

wherein $A^2$ is a phenyl group which may be substituted by a halogen atom, a lower alkyl group, a lower alkoxy group or a halogenated lower alkyl group; $R^4$ is a hydrogen atom, a straight or branched alkyl group which may be substituted by an alkoxy group or a halogen atom or a cycloalkyl group which may be substituted by an alkoxy group or a halogen atom; and X, Y and Z are the same or different and represent a hydrogen atom, a halogen atom, an alkyl group or an alkoxy group comprising reacting a styrene derivative of the formula (3):

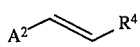

wherein $A^2$ and $R^4$ are the same as defined above, with a silane compound of the formula (4):

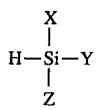

wherein X, Y and Z are the same as defined above, in the presence of a catalyst comprising a complex of a transition metal of Groups 8, 9 and 10 in the Periodic Table having an optically active substance of a tertiary phosphine compound (1) as a ligand.

DETAILED DESCRIPTION OF THE INVENTION

I. Tertiary phosphine compound (1)

In the tertiary phosphine compound (1), $R^1$ and $R^{1'}$ are hydrogen atoms or together form a group of the formula: —CH=CH—CH=CH—; $R^2$ and $R^3$ together form a group of the formula (a):

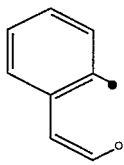

in which —● represent a bond to be bonded to the $R^3$ group, and —o represents a bond to be bonded to the $R^2$ group when $R^1$ and $R^{1'}$ together form a group of the formula: —CH=CH—CH=CH—, or when $R^1$ is a hydrogen atom, $R^2$ and $R^3$ together form a group of the formula: —CH=CH—CH=CH— or $R^2$ is a hydrogen atom and $R^3$ is an alkyl group having 1 to 6 carbon atoms in general which may be substituted by a halogen tom, a lower alkoxy group having 1 to 6 carbon atoms in general or a halogenated lower alkyl group having 1 to 6 carbon atoms in general, or a phenyl group which may be substituted by a halogen atom, a lower alkyl group having 1 to 6 carbon atoms in general or a halogenated lower alkyl group having 1 to 6 carbon atoms in general.

Examples of the alkyl group for $R^3$ are a methyl group, an ethyl group, a n-propyl group, an isopropyl group, a n-butyl group, a tert.-butyl group, etc.

Examples of the halogen atom, the lower alkoxy group, or the halogenated lower alkyl group as the optional substituent of the alkyl group for $R^3$ are a fluorine atom, a chlorine atom, a bromine atom, an iodine atom; a methoxy group, an ethoxy group, a propoxy group; or a monochloromethyl group, a dichloromethyl group, a trichloromethyl group, a fluoromethyl group, a trifluoromethyl group, a 2,2,2-trifluoroethyl group, etc.

Examples of the halogen atom, the lower alkyl group, the lower alkoxy group, or the halogenated lower alkyl group as the optional substituent of the phenyl group for $R^3$ are a fluorine atom, a chlorine atom, a bromine atom, an iodine atom; a methyl group, an ethyl group, a n-propyl group, an isopropyl group, a n-butyl group, a tert.-butyl group; a methoxy group, an ethoxy group, a propoxy group; or a monochloromethyl group, a dichloromethyl group, a trichloromethyl group, a fluoromethyl group, a trifluoromethyl group, a 2,2,2-trifluoroethyl group, etc.

The number of the substituents is not limited. The number of the substituents is usually from 1 to 3 in the alkyl group, while it is from 1 to 5 in the phenyl group. A position of the substituent is not limited.

$A^1$ is a 3-trifluoromethylphenyl group or a 3,5-bis(trifluoromethyl)phenyl group when $R^1$ is a hydrogen atom and $R^2$ and $R^3$ together form a group of the formula: —CH=CH—CH=CH—, or a phenyl group which may be substituted by a halogen atom, a lower alkyl group having 1 to 6 carbon atoms in general, a lower alkoxy group having 1 to 6 carbon atoms in general or a halogenated lower alkyl group having 1 to 6 carbon atoms in general when $R^1$ is not a hydrogen atom or when $R^2$ and $R^3$ do not together form a group of the formula: —CH=CH—CH=CH—.

Examples of the halogen atom as the optional substituent of the phenyl group for $A^1$ are a fluorine atom, a chlorine atom, a bromine atom and an iodine atom; examples of the lower alkyl group are a methyl group, an ethyl group, a n-propyl group, an isopropyl group, a n-butyl group, a tert.-butyl group, etc.; examples of the lower alkoxy group are a methoxy group, an ethoxy group, a propoxy group, etc.; and examples of the halogenated lower alkyl group are a monochloromethyl group, a dichloromethyl group, a trichloromethyl group, a fluoromethyl group, a trifluoromethyl group, a 2,2,2-trifluoroethyl group, etc.

The number of the substituent in $A^1$ is not limited. Usually, the number of the substituent is from 1 to 5. A position of the substituent is not limited.

The tertiary phosphine compound (1) of the present invention includes an optically active (+) and (−) isomers, and the present invention includes the (+) and (−) isomers and a racemic body.

Preparation of the phosphine compound (Ia)

Among the tertiary phosphine compound (I), a compound (Ia) corresponding to the formula (I) in which $R^1$ and $R^2$ together forms a group of the formula: —CH=CH—CH=CH— may be prepared by the following reaction scheme:

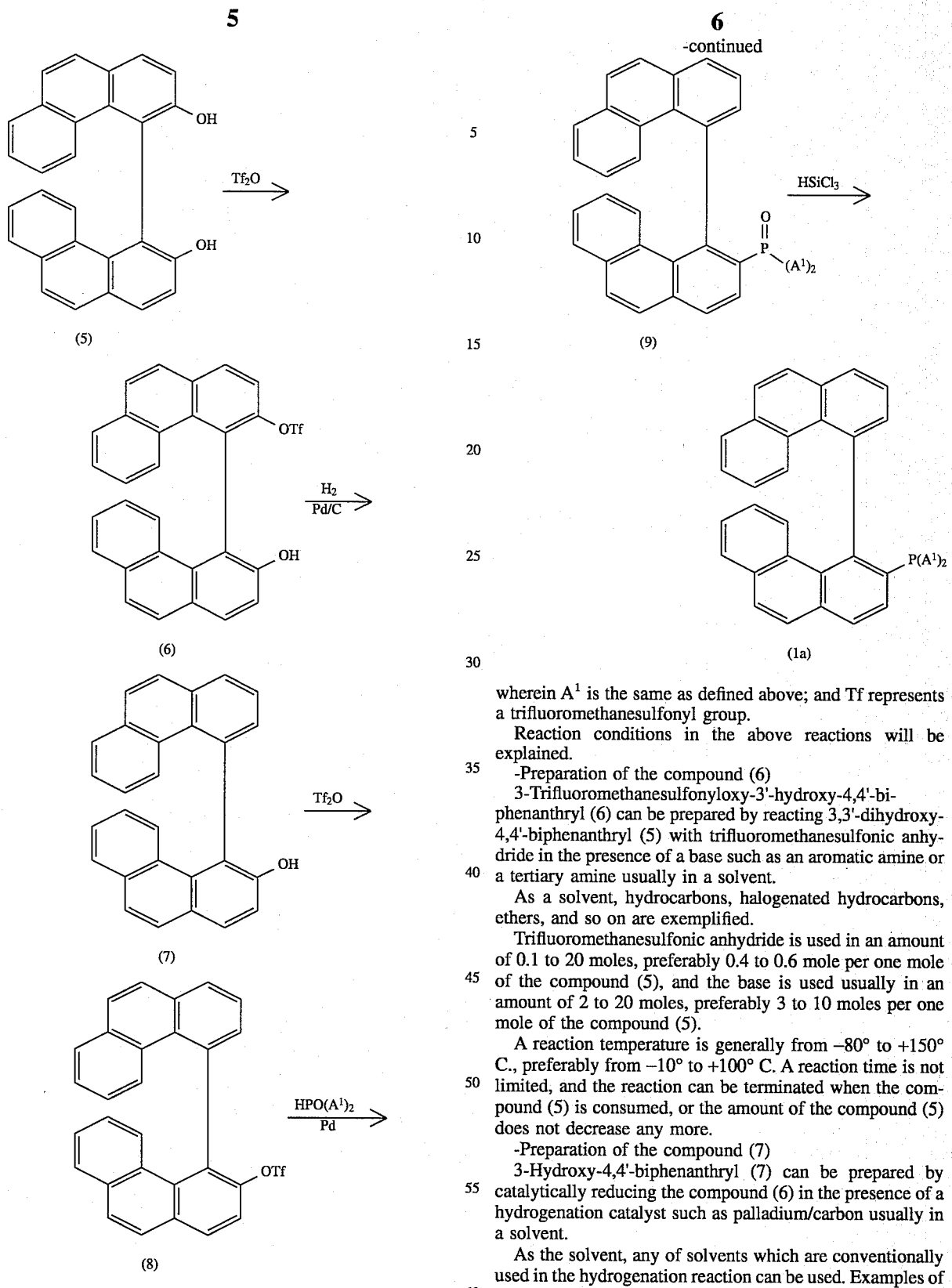

wherein $A^1$ is the same as defined above; and Tf represents a trifluoromethanesulfonyl group.

Reaction conditions in the above reactions will be explained.

-Preparation of the compound (6)

3-Trifluoromethanesulfonyloxy-3'-hydroxy-4,4'-biphenanthryl (6) can be prepared by reacting 3,3'-dihydroxy-4,4'-biphenanthryl (5) with trifluoromethanesulfonic anhydride in the presence of a base such as an aromatic amine or a tertiary amine usually in a solvent.

As a solvent, hydrocarbons, halogenated hydrocarbons, ethers, and so on are exemplified.

Trifluoromethanesulfonic anhydride is used in an amount of 0.1 to 20 moles, preferably 0.4 to 0.6 mole per one mole of the compound (5), and the base is used usually in an amount of 2 to 20 moles, preferably 3 to 10 moles per one mole of the compound (5).

A reaction temperature is generally from −80° to +150° C., preferably from −10° to +100° C. A reaction time is not limited, and the reaction can be terminated when the compound (5) is consumed, or the amount of the compound (5) does not decrease any more.

-Preparation of the compound (7)

3-Hydroxy-4,4'-biphenanthryl (7) can be prepared by catalytically reducing the compound (6) in the presence of a hydrogenation catalyst such as palladium/carbon usually in a solvent.

As the solvent, any of solvents which are conventionally used in the hydrogenation reaction can be used. Examples of the solvent are methanol, ethanol, isopropanol, dioxane, THF, dimethyl ether, dimethoxyethane, toluene, hexane, and a mixture of at least two of them.

An amount of the solvent is not critical.

A reaction temperature is generally from −150° to +200° C., preferably from −80° to +150° C. A reaction time is not limited, and the reaction can be terminated when the compound (6) is consumed, or the amount of the compound (6) does not decrease any more.

-Preparation of the compound (8)

3-Trifluoromethanesulfonyloxy-4,4'-biphenanthryl (8) can be prepared by reacting the compound (7) with trifluoromethanesulfonic anhydride in the presence of a base such as an aromatic amine or a tertiary amine usually in a solvent.

As a solvent, hydrocarbons, halogenated hydrocarbons, ethers, and so on are exemplified.

Trifluoromethanesulfonic anhydride is used usually in an amount of 0.1 to 20 moles, preferably 1 to 5 mole per one mole of the compound (7), and the base is used in an amount of 2 to 20 moles, preferably 3 to 10 moles per one mole of the compound (7).

A reaction temperature is from −80° to +150° C., preferably from −10° to +100° C. A reaction time is not limited, and the reaction can be terminated when the compound (7) is consumed, or the amount of the compound (7) does not decrease any more.

-Preparation of the compound (9)

The compound (9) can be prepared by reacting the compound (8) with a diarylphosphine oxide in the presence of a base such as a tertiary amine and a palladium-phosphine catalyst usually in a polar solvent.

Amounts of the base, the palladium-phosphine catalyst and the diarylphosphine oxide are usually from 1 to 20 moles, preferably from 5 to 10 moles; from 0.1 to 1 mole, preferably from 0.4 to 0.6 mole; and from 1 to 20 moles, preferably from 1 to 4 moles, respectively, per one mole of the compound (8).

A reaction temperature is generally from −80° to +200° C., preferably from 0° to +120° C. A reaction time is not limited, and the reaction can be terminated when the compound (8) is consumed, or the amount of the compound (8) does not decrease any more.

-Preparation of the compound (1a)

The compound (1a) can be prepared by reacting the compound (9) with a reducing agent such as trichlorosilane in the presence of a base such as a tertiary amine usually in a solvent.

Amounts of the base and the reducing agent are usually from 1 to 100 moles, preferably 40 to 60 moles; and from 1 to 50 moles, preferably from 1 to 20 moles, respectively, per one mole of the compound (9).

A reaction temperature is from −20° to +150° C., preferably from −10° to +100° C. A reaction time is not limited, and the reaction can be terminated when the compound (9) is consumed, or the amount of the compound (9) does not decrease any more.

-Preparation of the compound (1a')

The compound (1a') corresponding to the tertiary phosphine compound (1) of the present invention in which $R^1$ is a hydrogen atom, and $R^2$ and $R^3$ together form —CH=CH—CH=CH— can be prepared in the same manner as in the preparation of the compound (1a) except that 2,2'-dihydroxy-1,1'-binaphthyl (5') as a starting material in place of 3,3'-dihydroxy-4,4'-biphenanthryl (5).

In the preparation of the compound (1a) or (1a'), since the reaction of each step proceeds with maintaining a structure of the axial asymmetry of the substrates, an optically active compound (1a) or (1a') can be obtained as a final product when an optically active compound (5) or (5') is used as a starting compound. When a racemic compound (5) or (5') is used as a starting compound, a racemic compound (1a) or (1a') is obtained. According to the present invention, it is possible to obtain an optically active substance or a racemic substance according to the final use of the compound (1).

-Preparation of the compound (1b)

The compound (1b) corresponding to the tertiary phosphine compound (1) of the present invention in which $R^1$ and $R^2$ are both hydrogen atoms can be prepared by the following reaction scheme:

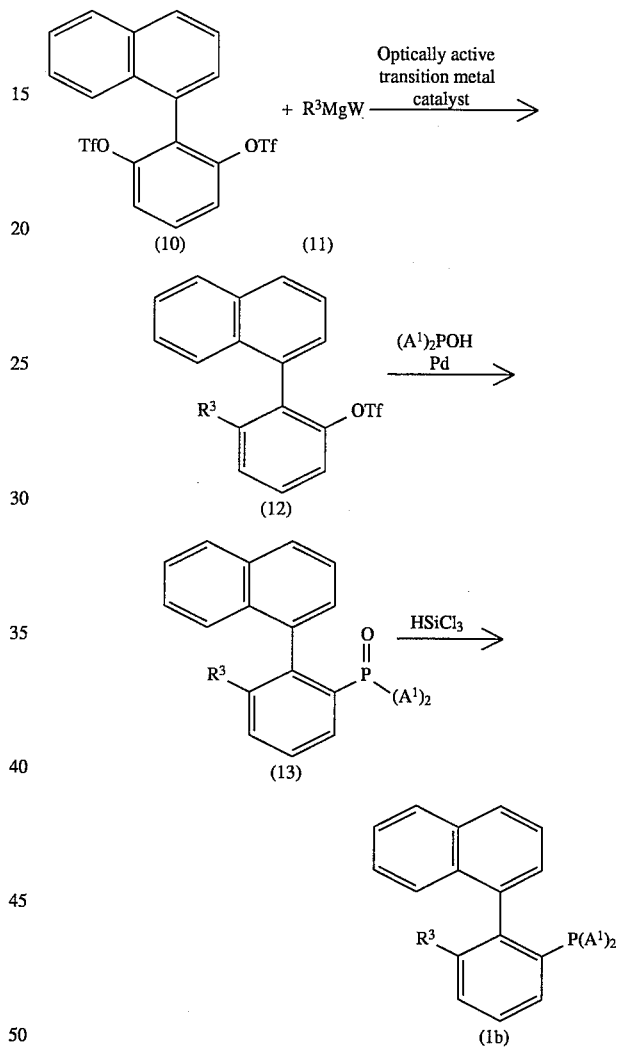

wherein Tf, $R^3$ and $A^1$ are the same as defined above, and W is a halogen atom.

The reaction conditions in the above reaction scheme will be explained.

-Preparation of the compound (12)

The compound (12) can be prepared by reacting the compound (10) and the compound (11) in the presence of an optically active transition metal catalyst.

An amount of the optically active transition metal catalyst is usually from 0.001 to 500 mole %, preferably from 0.01 to 20 mole % based on the mole of the compound (10).

This reaction is carried out in a solvent in general, optionally in the presence of a co-catalyst such as a metal halide or a base such as an organic base.

A reaction temperature is usually from −80° to +200° C., preferably from −10° to 150° C.

Examples of the compound (11) are methylmagnesium bromide, ethylmagnesium bromide, propylmagnesium bromide, phenylmagnesium bromide, 4-chlorophenylmagnesium bromide, 4-trifluoromethylphenylmagnesium bromide, and so on.

Examples of the metal halide to be used as the co-catalyst are halides of copper or lithium such as copper iodide, lithium bromide, lithium iodide, and so on.

An amount of the metal halide is usually from 0.1 to 500 mole %, preferably from 0.1 to 300 mole % based on the mole of the compound (10).

Examples of the organic base are organic amines such as triethylamine, diisopropylethylamine, tributylamine, DBU, dimethylaminopyridine, picoline, and so on.

An amount of the organic base is usually from 0.5 to 20 moles, preferably from 0.8 to 100 moles per one mole of the compound (10).

As the solvent to be used in the above reaction, any solvent can be used, as long as it is inert to the Grignard reagent. Examples of such solvent are dioxane, THF, diethyl ether, dimethoxyethane, toluene, hexane, dimethylaniline, and a mixture of at least two of them. An amount of the solvent is not critical.

A reaction temperature is usually from $-150°$ to $+200°$ C., preferably from $-80°$ to $+150°$ C. A reaction time is not limited, and the reaction can be terminated when the compound (10) is consumed, or the amount of the compound (10) does not decrease any more.

After the termination of the reaction, the reaction mixture is poured in water or acidic water to separate an organic layer, or the reaction mixture is extracted with an extraction solvent such as toluene, ethyl acetate, diethyl ether, dichloromethane, etc., and then the organic layer is separated and concentrated. If necessary, the product may be purified by column chromatography.

The optically active transition metal complex catalyst—to be used in the above reaction may be synthesized from a salt of a transition metal and an optically active ligand by a per se conventional method, for example, a method described in "Experimental Chemistry Lectures" (JIKKEN KAGAKU KOZA), 4th Edition, Vol. 18, "Organic Metal Complexes" (1991), page 393 (Maruzen). For example, the optically active transition metal complex catalyst can be obtained by ligand exchanging the salt of the transition metal and an optically asymmetric ligand compound and isolating the produced compound. Alternatively, the optically active transition metal complex catalyst can be formed in a reaction system of the compounds (10) and (11) and used as a catalyst without isolation.

The salt of the transition metal to be used herein is an organic or inorganic salt of divalent palladium which can be ligand exchanged with the phosphine base optically asymmetric ligand. Examples of such salt are sodium tetrachloropalladate (2), dichloro-bis(benzonitrile)palladium (2), ammonium tetrachloropalladate, and so on.

Examples of the of the optically active ligand are 1-diphenylphosphino-2-N,N-dimethylamino-3-phenylpropane (hereinafter referred to as "Phephos") and 1-diphenylphosphino-2-N,N-dimethylaminopropane, and the like, which are described in J. Org. Chem., 48, 2195 (1983). They may be optically active uni- or bidendate phosphine ligands.

-Preparation of the compound (13)

The compound (13) can be prepared by reacting the compound (12) with a diarylphosphine oxide in the presence of a base such as a tertiary amine, and a palladium/phosphine catalyst usually in a polar solvent such as dimethylsulfoxide.

Amounts of the base, the palladium/phosphine catalyst, and the diarylphosphine oxide are usually from 1 to 20 moles, preferably from 5 to 10 moles; from 0.1 to 1 mole, preferably from 0.4 to 0.6 mole; and from 1 to 10 moles, preferably from 2 to 4 moles, respectively, per one mole of the compound (12).

A reaction temperature is usually from $-20°$ to $+100°$ C., preferably from $0°$ to $+50°$ C. A reaction time is not limited, and the reaction can be terminated when the compound (12) is consumed, or the amount of the compound (12) does not decrease any more.

-Preparation of the compound (1b)

The compound (1b) can be prepared by reacting the compound (13) with a reducing agent such as trichlorosilane in the presence of a base such as a tertiary amine usually in a solvent.

Examples of the solvent are hydrocarbons, halogenated hydrocarbons, ethers, and so on.

Amounts of the base and the reducing agent are usually from 1 to 100 moles, preferably 40 to 60 moles, and from 1 to 50 moles, preferably from 10 to 20 moles, respectively, per one mole of the compound (13).

A reaction temperature is usually from $-20°$ to $+150°$ C., preferably from $-10°$ to $100°$ C. A reaction time is not limited, and the reaction can be terminated when the compound (13) is consumed, or the amount of the compound (13) does not decrease any more.

When either one of the (+) and (−) isomers of the optically active uni- or bidendate phosphine ligands is selected and the transition metal complex comprising such isomer as the ligand is used in the step of preparing the compound (12), either one isomer of the compound (12) having the intended absolute configuration is preferentially obtained. Since each of the steps after the preparation of the compound (12) proceeds with maintaining the axial asymmetry of the substrate, the compound (1b) having the intended absolute configuration can be preferentially obtained. When the racemic uni- or bidendate phosphine ligand is used, the racemic compound (1b) is obtained. According to the present invention, it is possible to obtain an optically active substance or a racemic substance according to the final use of the compound (1b).

II. Complexes of the 8 to 10 Groups transition metals comprising the tertiary phosphine compound as ligand The complex of the transition metal of the 8 to 10 groups comprising the tertiary phosphine compound (1) as the ligand can be prepared by coordinating the tertiary phosphine compound (1) on a transition metal.

Examples of the transition metal which forms such complex are metals of the 8 to 10 Groups such as palladium, rhodium, ruthenium, and the like.

Among the complexes, a palladium complex may be prepared by reacting dibenzonitrilepalladium dichloride with the tertiary phosphine compound (1) of the present invention according to the method described in "Experimental Chemistry Lectures" (JIKKEN KAGAKU KOZA), 4th Edition, Vol. 18, "Organic Metal Complexes" (1991), page 393 (Maruzen). In general, the tertiary phosphine compound (1) can be reacted with a transition metal compound such as an organic or inorganic salt to replace the ligand, followed by isolation of the resulting complex. Alternatively, the complex may be synthesized in a reaction system in which the complex is used as the catalyst and used in a further step without isolation.

The complexes of other transition metals can be prepared according to the methods which are disclosed in the following publications:

J. Am. Chem. Soc., 93, 2397 (1971),

J. Chem. Soc. Chem. Commun., 922 (1985),

J. Med. Chem., 31, 2277 (1988), the disclosure of which are hereby incorporated by reference, and

JP-A-61-63690.

Specific examples of such metal complexes are as follows:

[Rh(COD)(tertiary phosphine compound (1))]ClO$_4$,
Rh(COD)(tertiary phosphine compound (1))Cl,
[Rh(NBD)(tertiary phosphine compound (1))]Cl,
Rh(CO)Cl(tertiary phosphine compound (1)),
PdCl$_2$(tertiary phosphine compound (1)),
RuCl$_4$(tertiary phosphine compound (1))$_2$[N(C$_2$H$_5$)$_3$],
Ru(acac)$_2$(tertiary phosphine compound (1)),
[RuCl(p-cymene)(tertiary phosphine compound (1)]Cl,
wherein "COD" represents 1,5-cyclooctadiene, "NBD" represents norbornadiene, and "acac" represents acetyl acetonate.

As the transition metal compound to be used in the preparation of the transition metal complex, a zero-valency compound or cationic compound of the transition metal may be used, and examples of such compound are Rh(acac)(NBD), Rh(acac)(COD), Rh(acac)$_2$, [Rh(COD)Cl]$_2$, [Rh(NBD)Cl]$_2$, [Rh(C$_2$H$_4$)$_2$Cl]$_2$, [Rh(OCOCH$_3$)$_2$Cl]$_2$, [Rh(1,5-hexadiene)$_2$Cl]$_2$, and Ru(acac)$_3$.

When the transition metal complex having the optically active substance of the tertiary phosphine compound (1) as the ligand is used as a catalyst in the asymmetric synthesis reaction such as an asymmetric reduction, a desired product can be obtained in a high yield and a high asymmetric yield.

III. Preparation of the organic silicon compound: (2)

The optically active organic silane compound of the formula (2):

(2)

wherein $A^2$ is a phenyl group which may be substituted by a halogen atom, a lower alkyl group having 1 to 6 carbon atoms in general, a lower alkoxy group having 1 to 6 carbon atoms in general or a halogenated lower alkyl group having 1 to 6 carbon atoms in general; $R^4$ is a hydrogen atom, a straight or branched alkyl group having 1 to 6 carbon atoms in general which may be substituted by an alkoxy group or a halogen atom, or a cycloalkyl group having 3 to 6 carbon atoms in general which may be substituted by an alkoxy group or a halogen atom; and X, Y and Z are the same or different and represent a hydrogen atom, a halogen atom, an alkyl group having 1 to 4 carbon atoms in general or an alkoxy group having 1 to 4 carbon atoms in general can be prepared by reacting a styrene derivative of the formula (3):

(3)

wherein $A^2$ and $R^4$ are the same as defined above, with a silane compound of the formula (4):

(4)

wherein X, Y and Z are the same as defined above in the presence of a catalyst comprising the transition metal complex having the optically active substance of the tertiary phosphine compound (1) as the ligand.

Examples of the halogen atom as the optional substituent of the phenyl group for $A^2$ in the styrene derivative (3) are a fluorine atom, a chlorine atom, a bromine atom and an iodine atom; examples of the lower alkyl group are a methyl group, an ethyl group, a n-propyl group, an isopropyl group, a n-butyl group, a tert.-butyl group, etc.; examples of the lower alkoxy group are a methoxy group, an ethoxy group, a propoxy group, a butoxy group, etc.; and examples of the halogenated lower alkyl group are a monochloromethyl group, a dichloromethyl group, a trichloromethyl group, a fluoromethyl group, a trifluoromethyl group, a 2,2,2-trifluoroethyl group, etc.

The number of the substituent on the phenyl group of $A^2$ is not limited, and is from 1 to 5. A position of the substituent is not critical.

Examples of the straight or branched alkyl group for $R^4$ of the styrene derivative (3) are a methyl group, an ethyl group, a n-propyl group, an isopropyl group, a n-butyl group, an isobutyl group, etc., and examples of the cycloalkyl group are a cyclopentyl group, a cyclohexyl group, a cycloheptyl group, etc.

Examples of the alkoxyl group as the optional substituent on the straight or branched alkyl group or the cycloalkyl group are a methoxy group, an ethoxy group, a propoxy group, etc., and examples of the halogen atom are a fluorine atom, a chlorine atom, a bromine atom and an iodine atom.

Among the tertiary phosphine compounds (1), a compound of the formula (1) in which $A^2$ is a 3-trifluoromethylphenyl group or a 3,5-bis(trifluoromethyl)phenyl group is preferred, since an optical yield of the product is increased. In particular, the compound of the formula (1) in which $A^2$ is a 3,5-bis(trifluoromethyl)phenyl group is more preferred, since a reaction time can be shortened.

The tertiary phosphine compound (1) according to the present invention is present both in the forms of the (+) isomer and the (−) isomer. Then, the organic silane compound prepared using the (+) isomer and that prepared using the (−) isomer are in the relationship of enantiomers. Then, either one of the (+) and (−) isomers is selected and used in accordance with a configuration of the desired organic silicon compound.

When palladium is used as the transition metal on which the phosphine compound (1) is coordinated, the reaction proceeds at a high stereoselectivity.

In the silane compound of the formula (4), examples of the alkyl group for X, Y and Z are a methyl group, an ethyl group, a propyl group, etc.; examples of the alkoxy group are a methoxy group, an ethoxy group, a propoxy group, etc.; and examples of the halogen atom are a chlorine atom, a bromine atom, etc.

Among the silane compounds (4), trichlorosilane is preferred, since the hydrosilylation reaction proceeds quickly.

The hydrosilylation reaction is carried out in the presence or absence of a solvent. When the solvent is used, a hydrocarbon, a halogenated hydrocarbon or an ether is preferably used.

An amount of the transition metal complex is usually from 0.001 to 1 mole %, preferably from 0.01 to 0.1 mole % based on the mole of the styrene derivative (3). A molar ratio of the tertiary phosphine compound to the transition metal in the transition metal complex is from 1:1 to 3:1, preferably around 2:1.

An amount of the silane compound (4) is usually from 1 to 3 moles, preferably from 1 to 1.2 moles per one mole of the styrene derivative (3).

A reaction temperature is usually from −50° to +150° C., preferably from −20° to +40° C.

A manner of addition of the styrene derivative (3) and the silane compound (4) is not critical, and either one of the styrene derivative (3) and the silane compound (4) may be added prior to the other, or they may be added at the same time.

After the reaction, the desired compound is recovered by conventional post-treatment such as distillation to remove the unreacted raw materials, or filtration to remove the metals. A pure product can be isolated by subjecting the reaction mixture to a known purification treatment such as distillation, column chromatography, and so on.

The obtained optically active organic silicon compound (2) can be converted to a corresponding alcohol with maintaining its configuration. For example, in the case of a trichlorosilyl compound, that is, the compound of the formula (2) in which X, Y and Z are all chlorine atoms, the silyl group is converted to a hydroxy group by reacting the compound with hydrogen peroxide in a mixed solvent of tetrahydrofuran and methanol in the presence of potassium bicarbonate. Other optically active organic silicon compounds may be converted to the corresponding alcohols according to the methods described in, for example, J. Organometallic Chem., 269. (1984) C37–C39, and J. Org. Chem., 1987, 52, 4412–4, the disclosures of which are hereby incorporated by reference.

As explained above, the tertiary phosphine compound (1) of the present invention is particularly useful as the ligand of the transition metal complex which has an excellent catalytic activity in various asymmetric hydrosilylation reactions.

When the transition metal complex having the optically active substance of the tertiary phosphine compound (1) as the ligand is used as a catalyst in the asymmetric hydrosilylation reaction of the styrene derivative, the desired optically active organic silicon compound, which may be useful as an important intermediate in the preparation of various optically active compounds, is obtained at the high yield and the high selectivity.

PREFERRED EMBODIMENTS OF THE INVENTION

The present invention will be illustrated by the following Examples, which do not limit the scope of the present invention in any way.

In the Examples, analyses were carried out using the following equipments:

Polarimeter: DIP-370 type (manufactured by JAPAN SPECTROSCOPIC GO., LTD.)

$^1$H-NMR spectrum: JNM-EX 270 type (270 MHz, manufactured by JOEL LTD.); internal standard: tetramethylsilane $^{31}$P-NMR spectrum: JNM-EX 270 type (109 Hz, manufactured by JOEL LTD.), external standard: phosphoric acid.

REFERENCE EXAMPLE

Racemic 3,3'-dihydroxy-4,4'-biphenanthryl was synthesized according to the method disclosed in J. Chem. Soc., Chem. Commun., 1065 (1985), the disclosure of which is hereby incorporated by reference.

The racemic mixture (6.1 g) was subjected to optical resolution by HPLC (column: Sumichiral OA-2000 manufactured by Sumika Chemical Analysis Service Ltd.; moving phase: n-hexane/1,2-dichloroethane/ethanol=80/15/5 (by volume); UV-light detector: wavelength of 254 nm) to obtain (R)-(–)-3,3'-dihydroxy-4,4'-biphenanthryl and (S)-(+)- 3,3'-dihydroxy-4,4'-biphenanthryl (each 2.9 g). Their optical purities were 99.9%ee and 99.5%ee, respectively.

EXAMPLE 1-(1)

In a solution of (R)-(–)-3,3'-dihydroxy-4,4'-biphenanthryl (1.89 g, 4.89 mmol) and pyridine (1.00 ml, 12.4 mmol) in dichloromethane cooled with ice, trifluoromethanesulfonic anhydride (1.38 g, 4.89 mmol) was dropwise added. After stirring the mixture at 0° C. for one hour, the solvent was evaporated off. The residue was diluted with ethyl acetate (50 ml) and washed with 5% hydrochloric acid, a saturated aqueous solution of sodium hydrogencarbonate and a saturated aqueous solution of sodium chloride successively. The organic layer was dried over anhydrous sodium sulfate, and the solvent was evaporated off to obtain a crude product.

Then, the crude product was purified by silica gel column chromatography (developing phase: dichloromethane) to obtain (R)-3-trifluoromethanesulfonyloxy-3'-hydroxy-4,4'-biphenanthryl (2.05 g).

Yield, 81%. Elementary analysis: $C_{29}H_{17}O_4SF_3$ Calculated: C, 67.18%; H, 3.30% Found: C, 67.15%; H, 3.38%.

EXAMPLE 1-(2)

In a suspension of 10% palladium/carbon (120 mg) in ethanol (5 ml), (R)-3-trifluoromethanesulfonyloxy-3'-hydroxy-4,4'-biphenanthryl (580 mg, 1.12 mmol) and diisopropylamine (290 mg, 2.24 mmol) were added at room temperature, and reacted in a hydrogen atmosphere (1 atm.) for 10 hours.

After confirming the consumption of the raw materials by TLC (thin layer chromatography), the reaction mixture was filtrated through a celite filter, and a filtrate was concentrated to obtain a crude product. The crude product was then purified by silica gel column chromatography (developing phase: n-hexane/ethyl acetate=6/1) to obtain (S)-3-hydroxy-4,4'-biphenanthryl (410 mg).

Yield, 99%.

EXAMPLE 1-(3)

To an ice-cooled solution of (S)-3-hydroxy-4,4'-biphenanthryl (370 mg, 1.0 mmol) and pyridine (0.2 ml, 2.47 mmol) in dichloromethane, trifluoromethanesulfonic anhydride (0.2 ml, 1.19 mmol) was dropwise added. After stirring the mixture at 0° C. for two hours, the solvent was evaporated off. The residue was diluted with ethyl acetate (50 ml) and washed with 5% hydrochloric acid, a saturated aqueous solution of sodium hydrogencarbonate and a saturated aqueous solution of sodium chloride successively. The organic layer was dried over anhydrous sodium sulfate, and the solvent was evaporated off to obtain a crude product.

Then, the crude product was purified by silica gel column chromatography (developing phase: dichloromethane)to obtain (S)-3-trifluoromethanesulfonyloxy-4,4'-biphenanthryl (482 mg).

Yield, 96%,

EXAMPLE 1-(4)

Under a nitrogen atmosphere, in a solution of diisopropylethylamine (475 mg, 3.7 mmol) in dimethylsulfoxide (4 ml), (S)-3-trifluoromethanesulfonyloxy-4,4'-biphenanthryl (462 mg, 0.92 mmol), diphenylphosphine oxide (372 mg, 1.84 mmol), palladium acetate (41 mg, 0.18 mmol) and 1,4-bis(diphenylphosphino)butane (78 mg, 0.18 mmol) were added, and the mixture was stirred at 100° C. for 10 hours. After cooling, the reaction mixture was concentrated under reduced pressure, and the residue was diluted with ethyl acetate (50 ml) and washed with 5% hydrochloric acid, a saturated aqueous solution of sodium hydrogencarbonate and a saturated aqueous solution of sodium chloride successively. The organic layer was dried over anhydrous sodium sulfate, and the solvent was evaporated off to obtain a crude product.

Then, the crude product was purified by silica gel column chromatography (developing phase: n-hexane/ethyl acetate=1/1) to obtain (S)-3-diphenylphosphinyl-4,4'-biphenanthryl (433 mg).

Yield, 85%. Optical rotation: $[\alpha]_D^{22}$=−69.6 (C=0.55, CHCl$_3$).

EXAMPLE 1-(5)

Under a nitrogen atmosphere, in a solution of (S)-3-diphenylphosphinyl-4,4'-biphenanthryl (172 mg, 0.31 mmol) and triethylamine (1.23 g, 12.1 mmol) in toluene (5 ml), trichlorosilane (61.7 mg, 4.55 mmol) was added at 0° C., and then heated to 100° C. and stirred at that temperature for 15 hours. After cooling to room temperature, the reaction mixture was diluted with diethyl ether, and a small amount of a saturated aqueous solution of sodium hydrogencarbonate was added to stop the reaction. Then, the reaction mixture was filtrated through a celite filter, and washed with diethyl ether. The combined filtrate and diethyl ether phase were dried over anhydrous magnesium sulfate, and the solvent was evaporated off to obtain a crude product.

Then, the crude product was purified by silica gel column chromatography (developing phase: n-hexane/dichloromethane=1/1) to obtain (S)-3-diphenylphosphino-4,4'-biphenanthryl (152 mg).

Yield, 91%. Optical rotation: $[\alpha]_D^{22}$=+267.5 (C=0.40, CHCl$_3$).

EXAMPLE 2-(1)

Under a nitrogen atmosphere, trichlorosilane (0.25 ml, 2.5 mmol) was added to a mixture of allylpalladium chloride dimer (0.42 mg, 1.15 μmol corresponding to 2.3 μmol of palladium), (S)-3-diphenylphosphino-4,4'-biphenanthryl (2.48 mg, 4.6 μmol) and styrene (214 mg, 2.05 mmol) at 0° C. while stirring, followed by further stirring for 12 hours.

After confirming complete consumption of styrene by gas chromatography and $^1$H-NMR, the reaction mixture was concentrated under reduced pressure to obtain 1-phenyl-1-trichlorosilylethane (490 mg).

Yield, >99%.

An optical purity of the product was determined by converting its trichlorosilyl group to a hydroxy group with maintaining its configuration, changing the compound to 3,5-dinitrophenyl carbamate, and then subjecting it to LC (liquid chromatography) analysis using a column for isolating optical isomers.

EXAMPLE 2-(2)

Potassium fluoride (690 mg, 11.9 mmol) and potassium hydrogencarbonate (1.76 g, 17.6 mmol) were suspended in a mixed solvent of THF (100 ml) and methanol (100 ml). To the ice-cooled suspension, 1-phenyl-1-trichlorosilylethane (460 mg, 1.9 mmol) was dropwise added while stirring, followed by the addition of 30% aqueous hydrogen peroxide (2 ml, 19 mmol). After stirring at room temperature for 11 hours, excessive hydrogen peroxide was reduced with a saturated aqueous solution of sodium thiosulfate (2 ml), and then the reaction mixture was filtrated through a celite filter, and washed with dichloromethane. The filtrated was concentrated and phase separated. The aqueous layer was extracted with dichloromethane (each 10 ml) three times. After the combined organic layer was dried over anhydrous sodium sulfate, the solvents were evaporated off.

The obtained crude product was purified by silica gel column chromatography (developing phase: n-hexane/ethyl acetate=5/1) to obtain (R)-1-phenethyl alcohol (224 mg).

Yield, 95%. Optical rotation: $[(\alpha]_D^{22}$=−34.6 (C=1.85, CH$_2$Cl$_2$).

EXAMPLE 2-(3)

Optically active phenethyl alcohol obtained in Example 2-(2) was converted to 3,5-dinitrophenyl carbamate by a per se conventional method. Then, its optical purity was determined by subjecting the carbamate to HPLC (column: Sumichiral OA-4700 manufactured by Sumika Chemical Analysis Service Ltd.; developing phase: n-hexane/1,2-dichloroethane/ethanol=50/15/1 ) and found to be 71%ee.

REFERENCE EXAMPLE 2

(S)-2-Diphenylphosphino-1,1'-binaphthyl was synthesized by the method described in Tetrahedron, 50, 4293 (1994), the disclosure of which is hereby incorporated by reference.

EXAMPLE 3

In the same manner as in Example 2 except that (S)-2-diphenylphosphino-1,1'-binaphthyl was used in place of (S)-3-diphenylphosphino-4,4'-biphenanthryl, the reactions were carried out to obtain (R)-1-phenyl-1-trichlorosilylethane. Optical purity, 93%ee.

EXAMPLES 4–8

In the same manner as in Example 3 except that each compound shown in Table 1 was used in place of styrene, the reactions were carried out to obtain a desired optically active organic silicon compound (2).

TABLE 1

| Ex. No. | Raw material styrene derivative (1) | Optically active organic silicon compound (4) | Optical purity (% ee) |
| --- | --- | --- | --- |
| 4 | 4-Trifluoromethylphenylethene | 1-(4-Trifluoromethylphenyl)-1-trichlorosilylethane | 96 (R-isomer) |
| 5 | 3-Trifluoromethylphenylethene | 1-(3-Trifluoromethylphenyl)-1-trichlorosilylethane | 95 (R-isomer) |
| 6 | 4-Chlorophenylethene | 1-(4-Chlorophenyl)-1-trichlorosilylethane | 94 (R-isomer) |
| 7 | 3-Chlorophenylethene | 1-(3-Chlorophenyl)-1-trichlorosilylethane | 95 (R-isomer) |
| 8 | 1-Phenyl-1-hexene | 1-Phenyl-1-trichlorosilylhexane | 92 (R-isomer) |

COMPARATIVE EXAMPLE 1

In the same manner as in Example 3 except that (R)-2-methoxy-2'-diphenylphosphino-1,1'-binaphthyl in place of (S)-2-diphenylphosphino-1,1'-binaphthyl, the reactions were carried out to obtain (R)-1-phenyl-1-trichlorosilylethane having an optical purity of only 14%ee.

EXAMPLE 9

In the same manner as in Example 1 except that (R)-2,2'-dihydroxy-1,1'-binaphthyl was used in place of (R)-(−)-3,3'-dihydroxy-4,4'-biphenanthryl, and bis[3,5-bis(trifluoromethyl)phenyl]phosphine oxide was used in place of diphenylphosphine oxide, the reactions were carried out to obtain (S)-2-bis[3,5-bis(trifluoromethyl)phenyl]phosphino-1,1'-binaphthyl in a yield of 54%.

Optical rotation: $[\alpha]_D^{22}=+22.2$ (C=0.765, CHCl$_3$). $^1$H-NMR (CDCl$_3$): δ(ppm)=6.86–8.03 (m, aromatic). $^{31}$P-NMR (CDCl$_3$): δ(ppm)=−11.2 (s).

EXAMPLE 10

In the same manner as in Example 1 except that (R)-2,2'-dihydroxy-1,1'-binaphthyl was used in place of (R)-(−)-3,3'-dihydroxy-4,4'-biphenanthryl, and bis(3-trifluoromethylphenyl)phosphine oxide was used in place of diphenylphosphine oxide, the reactions were carried out to obtain (S)-2-bis(3-trifluoromethyl-phenyl)phosphino-1,1'-binaphthyl in a yield of 60%.

Optical rotation: $[\alpha]_D^{20}=+53.7$ (C=1.11, CHCl$_3$). $^1$H-NMR (CDCl$_3$): δ(ppm)=7.01–8.00 (m, aromatic). $^{31}$P-NMR (CDCl$_3$): δ(ppm)=−12.7 (s).

EXAMPLES 11–15

In the same manner as in Example 2 except that each optically active tertiary phosphine compound (1) shown in Table 2 was used in place of (S)-3-diphenylphosphino-4,4'-biphenanthryl, the reactions were carried out to obtain optically active 1-phenyl-1-trichlorosilylethane.

TABLE 2

| Ex. No. | Optically active tertiary phosphine compound (1) | Reaction time (hrs) | 1-Phenyl-1-trichlorosilylethane Yield (%) | 1-Phenyl-1-trichlorosilylethane Optical purity (% ee) |
|---|---|---|---|---|
| 11 | (S)-2-Bis[3,5-bis(trifluoromethyl)phenyl]phosphino-1,1'-binaphthyl | 1 | 88 | 97 (R-isomer) |
| 12 | (S)-2-Bis(3-trifluoromethylphenyl)phosphino-1,1'-binaphthyl | 15 | 81 | 95 (R-isomer) |
| 13 | (S)-2-Bis(4-trifluoromethylphenyl)phosphino-1,1'-binaphthyl | 11 | 92 | 93 (R-isomer) |
| 14 | (S)-2-Bis(4-fluorophenyl)-phosphino-1,1'-binaphthyl | 15 | 90 | 93 (R-isomer) |
| 15 | (S)-2-Bis(4-methoxyphenyl)-phosphino-1,1'-binaphthyl | 14 | 89 | 92 (R-isomer) |

EXAMPLES 16–22

In the same manner as in Example 11 except that each styrene derivative shown in Table 3 was used in place of styrene, the reactions were carried out to obtain an optically active organic silicon compound (2).

TABLE 3

| Ex. No. | Styrene derivatives | Optically active organic silicon compound (4) | Optical purity (%) |
|---|---|---|---|
| 16 | 4-Methoxyphenylethene | 1-(4-Methoxyphenyl)-1-trichlorosilylethane | 97 (R-isomer) |
| 17 | 4-Chlorophenylethene | 1-(4-Chlorophenyl)-1-trichlorosilylethane | 98 (R-isomer) |
| 18 | 1-Phenylpropene | 1-Phenyl-1-trichlorosilylpropane | 98 (R-isomer) |
| 19 | 4-Bromophenylethene | 1-(4-Bromophenyl)-1-trichlorosilylethane | 97 (R-isomer) |
| 20 | 4-Methylphenylethene | 1-(4-Methylphenyl)-1-trichlorosilylethane | 94 (R-isomer) |
| 21 | 2-Methylphenylethene | 1-(2-Methylphenyl)-1-trichlorosilylethane | 97 (R-isomer) |
| 22 | 3-Nitrophenylethene | 1-(3-Nitrophenyl)-1-trichlorosilylethane | 98 (R-isomer) |

REFERENCE EXAMPLE 3(1)

In a solution of 1,3-dimethoxybenzene (3.0 g, 21.7 mmol) dissolved in diethyl ether (90 ml), a 1.65M solution of n-butyl lithium in n-hexane (19.8 ml, 32.7 mmol of n-butyl lithium) was added at room temperature, and a reaction mixture was heated to reflux for 4 hours. After cooling the reaction mixture to 0° C., a solution of carbon tetrabromide (15.8 g, 47.7 mmol) in diethyl ether (60 ml) was added to the mixture, and stirred at room temperature for 20 hours. A small amount of water was added to the reaction mixture, and then the reaction mixture was diluted with ethyl acetate (90 ml). The organic layer was washed with water and dried over anhydrous magnesium sulfate. Thereafter, the solvent was evaporated off, and the residue was purified by column chromatography to obtain 1-bromo-2,6-dimethoxybenzene (2.70 g).

Yield, 57%. Elementary analysis: $C_8H_9O_2Br$ Calculated: C, 44.23%; H. 4.15% Found: C, 44.02%; H. 4.23%.

REFERENCE EXAMPLE 3-(2)

To a solution of 1-bromonaphthalene (10 g, 48 mmol) in THF (100 ml), a 1.65 M solution of n-butyl lithium in n-hexane (58 ml, 96 mmol of n-butyl lithium) and stirred at −78° C. for one hour. Then, trimethoxyborane (10 g, 96 mmol) was added, and the mixture was stirred at −78° C. for 30 minutes, and then at room temperature for one hour. To the mixture, phenothiazine (132 mg) and then a mixture of conc. hydrochloric acid (20 ml), phosphoric acid (30 ml) and water (220 ml) were gradually added. After heating the mixture to room temperature and stirring it for 20 hours, the organic layer was separated. The aqueous solution was washed with diethyl ether. The combined organic layer was washed with a 10% aqueous solution of sodium chloride. To the ice-cooled organic layer, a 5% aqueous solution of sodium hydroxide was added and stirred. Then, the mixture was phase separated, and the aqueous layer was saturated with sodium chloride, acidified with phosphoric acid, and extracted with diethyl ether. The diethyl ether layer was dried over anhydrous magnesium sulfate. The solvent was evaporated off, and the obtained solid residue was recrystallized from ethyl acetate/n-hexane to obtain naphthylboric acid (4.20 g).

Yield, 51%. Elementary analysis: $C_{10}H_9O_2B$ Calculated: C, 69.77%; H. 5.26% Found: C, 69.62%; H. 5.32%.

REFERENCE EXAMPLE 3-(3)

To a solution of 1-bromo-2,6-dimethoxybenzene, (2.63 g, 12.1 mmol), tetrakis(triphenylphosphine)palladium (0) (0.91 g, 0.76 mol) and 1-naphthylboric acid (4.16 g, 23.9 mmol) in 1,4-dioxane (160 ml), a 2N aqueous solution of sodium hydroxide (13 ml) was added, and the mixture was heated to reflux. After cooling, the solvent was evaporated off, and the residue was dissolved in diethyl ether. The diethyl ether solution was washed with water and dried over anhydrous magnesium sulfate. Then, the solvent was evaporated off, and the residue was purified by silica gel column chromatography (developing phase: n-hexane/ethyl acetate= 5/1) to obtain 1-naphthyl-2,6-dimethoxybenzene (2.50 g).

Yield, 79%. Elementary analysis: $C_{18}H_{16}O_2$ Calculated: C, 81.73%; H. 6.05% Found: C, 81.64%; H. 6.18%.

REFERENCE EXAMPLE 3-(4)

To a solution of 1-naphthyl-2,6-dimethoxybenzene (2.0 g, 7.5 mmol) in methylene chloride (30 ml), boron tribromide (1.7 ml, 17.5 mmol) was added at −78° C. The mixture was stirred for 20 hours with slowly warming the mixture to room temperature.

After decomposing excessive boron tribromide by the addition of a small amount of water, diethyl ether (300 ml) was added to the mixture. The organic layer was washed with water and dried over anhydrous magnesium sulfate. The solvent was evaporated off under reduced pressure, The residue was purified by silica gel column chromatography (developing phase: n-hexane/ethyl acetate=5/1) to obtain 1-naphthyl-2,6-dihyroxybenzene (1.70 g).

Yield, 95%. Elementary analysis: $C_{16}H_{12}O_2$ Calculated: C, 81.26%; H. 5.08% Found: C, 81.04%; H. 5.19%.

REFERENCE EXAMPLE 3-(5)

To a solution of 1-naphthyl-2,6-dihydroxybenzene (1.1 g, 4.66 mmol) in methylene chloride (10 ml), pyridine (1.06 ml) was added. To the ice-cooled mixture, trifluoromethanesulfonic anhydride (1.62 ml, 9.6 mmol) was added, and stirred for 6 hours. The reaction mixture was diluted with diethyl ether, and washed with 10% hydrochloric acid, a saturated aqueous solution of sodium hydrogencarbonate, and a saturated aqueous solution of sodium chloride, followed by drying over anhydrous magnesium sulfate. The solvent was removed off under reduced pressure, and the residue was purified by silica gel column chromatography (developing phase: n-hexane/ethyl acetate=5/1) to obtain 1-naphthyl-2,6-bis(trifluoromethanesufonyloxy)benzene (2.05 g).

Yield, 88%. Elementary analysis: $C_{18}H_{10}O_6S_2F_6$ Calculated: C, 43.16%; H. 2.00% Found: C, 43.01%; H. 2.21%.

EXAMPLE 23-(1)

Lithium bromide (174 mg, 2.00 mmol) which had been heat dried under reduced pressure, PdCl$_2$[(S)-Phephos] (49.4 mg, 0.094 mmol) and 1-naphthyl-2,6-bis(trifluoromethanesulfonyloxy)benzene (955 mg, 1.98 mmol) were dissolved in toluene (2.6 ml), and a 1.8N solution of phenylmagnesium bromide in ether (2.4 ml) was added to the solution at −20° C., followed by stirring for 26 hours at the same temperature. After adding 10% hydrochloric acid, the mixture was extracted with diethyl ether, and the organic layer was washed with a saturated aqueous solution of sodium chloride.

After evaporating the solvent off, the residue was purified by silica gel column chromatography (developing phase: n-hexane/ethyl acetate=5/1), and recrystallized from n-hexane to obtain (S)-(−)-2-naphthyl-3-trifluoromethanesulfonyloxybiphenyl (666 mg).

Yield, 78%. Optical purity, >99%ee. Melting point: 142° C. Optical rotation: $[\alpha]_D^{20}$=−145 (C=1.00, CHCl$_3$).

EXAMPLE 23-(2)

To a solution of diisopropylethylamine (270 mg, 2.08 mmol) in dimethylsulfoxide (1 ml), (S)-(−)-2-naphthyl-3-trifluoromethanesulfonyloxybiphenyl (108 mg, 0.252 mmol), diphenylphosphine oxide (106 mg, 0.522 mmol), palladium acetate (2.9 mg, 0.013 mmol) and 1,4-bis(diphenylphosphino)butane (5.6 mg, 0.013 mmol) were added and stirred at 100° C. for 12 hours. After cooling, the solvent was evaporated off, and the residue was diluted with ethyl acetate and washed with dilute hydrochloric acid and a saturated aqueous solution of sodium hydrogencarbonate. After the organic layer was dried over anhydrous magnesium sulfate, the solvent was evaporated off to obtain a crude product.

The crude product was purified by silica gel column chromatography (developing phase: n-hexane/ethyl acetate= 1/1) to obtain (S)-(+)-2-naphthyl-3-diphenylphosphinylbiphenyl (120 mg).

Yield, 99%. Melting point: 179° C. Optical rotation: $[\alpha]_D^{20}$=+49.2 (C=1.00, CHCl$_3$). $^1$H-NMR (CDCl$_3$): δ(ppm)=6.73–6.80 (m, 2H), 6.84–6.87 (m, 4H), 6.95–6.99 (m, 4H), 7.04–7.10 (m, 1H), 7.18–7.39 (m, 8H), 7.49–7.55 (m, 1H), and 7.60–7.69 (m, 5H). $^{31}$P-NMR (CDCl$_3$): δ(ppm)=28.0 (s).

EXAMPLE 23-(3)

To a solution of (S)-(+)-2-naphthyl-3-diphenyl-phosphinylbiphenyl (120 mg, 0.250 mmol) and triethylamine (1 ml) in toluene (6 ml), trichlorosilane (300 μl, 0.297 mmol) was added at 0° C. The mixture was heated to 130° C., and stirred for 36 hours at the same temperature. After cooling to room temperature, the reaction mixture was diluted with diethyl ether, and then the reaction was stopped by the addition of a small amount of a saturated aqueous solution of sodium hydrogencarbonate. Then, the mixture was filtrated through a celite filter, and washed with diethyl ether. The combined filtrate and diethyl ether phase were dried over anhydrous magnesium sulfate, and the solvent was evaporated off to obtain a crude product.

The crude product was purified by silica gel column chromatography (developing phase: n-hexane/ethyl acetate= 5/1) to obtain (S)-(+)-2-naphthyl-3-diphenylphosphinobiphenyl (85.0 mg).

Yield, 73%. Optical rotation: $[\alpha]_D^{20}$=+15.3 (C=0.5, CHCl$_3$). $^1$H-NMR (CDCl$_3$): δ(ppm)=6.84–7.03 (m, 6H), 7.06–7.39 (m, 15H), 7.44–7.54 (m, 2H), and 7.58–7.69 (m, 2H). $^{31}$P-NMR (CDCl$_3$): δ(ppm)=−12 5 (s).

EXAMPLE 24-(1)

Under a nitrogen atmosphere, trichlorosilane (0.30 ml, 3.0 mmol) was added to a mixture of (S)-(+)-2-naphthyl-3-diphenyl-phosphinobiphenyl (2.51 mg, 5.4 mmol) which was obtained in Example 1, allylpalladium chloride dimer (0.54 mg, 1.5 μmol corresponding to 3.0 μmol of palladium) and styrene (264 mg, 2.54 mmol) at 0° C. while stirring, followed by further stirring for 24 hours at the same temperature.

After confirming complete consumption, of styrene by gas chromatography and $^1$H-NMR, the reaction mixture was distilled with a Kugel rohr (bulbed tube) to obtain 1-phenyl-1-trichlorosilylethane (518 mg).

Yield, 85%. $^1$H-NMR (CDCl$_3$): δ(ppm)=1.62 (d, J=7.6 Hz, 3H), 2.90 (q, J=7.6 Hz, 1H), and 7.21–7.37 (m, 5H).

An optical purity of the product was determined by converting its trichlorosilyl group to a hydroxy group with maintaining its configuration, changing the compound to 3,5-dinitrophenyl carbamate, and then subjecting it to LC (liquid chromatography) analysis using a column for isolating optical isomers as described below.

EXAMPLE 24-(2)

Potassium fluoride (764 mg, 29.4 mmol) and potassium hydrogencarbonate (2.61 g, 26.0 mmol) were suspended in a mixed solvent of THF (50 ml) and methanol (50 ml). To the ice-cooled suspension, 1-phenyl-1-trichlorosilylethane (518 mg, 2.16 mmol) was dropwise added while stirring, followed by the addition of 30% aqueous hydrogen peroxide (2.2 ml). After stirring at room temperature for 11 hours, excessive hydrogen peroxide was reduced with a saturated aqueous solution of sodium thiosulfate (3 ml), and then the reaction mixture was filtrated through a celite filter, and washed with dichloromethane. The filtrate was concentrated and phase separated. The aqueous layer was extracted with dichloromethane (each 10 ml) three times. After the combined organic layer was dried over anhydrous sodium sulfate, the solvents were evaporated off.

The obtained crude product was purified by silica gel column chromatography (developing phase: n-hexane/ethyl acetate=5/1) to obtain (R)-1-phenethyl alcohol (196 mg).

Yield, 74%. $^1$H-NMR (CDCl$_3$): δ(ppm)=1.50 (d, J=6.3 Hz, 3H), 1.78 (brs, 1H), 4.90 (q, J=6.3 Hz, 1H) and 7.24–7.40 (m, 5H).

EXAMPLE 24-(3)

Optically active phenethyl alcohol obtained in Example 24-(2) was converted to 3,5-dinitrophenyl carbamate by a per se conventional method. Then, its optical purity was determined by subjecting the carbamate to HPLC (column: Sumichiral OA-4700 manufactured by Sumika Chemical Analysis Service Ltd.; developing phase: n-hexane/1,2-dichloroethane/ethanol=50/15/1) and found to be 91%ee.

What is claimed is:

1. A tertiary phosphine compound of the formula (1):

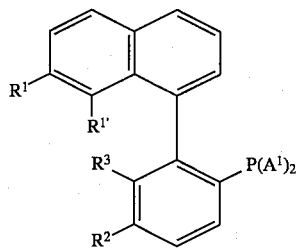
(1)

wherein R$^1$ and R$^{1'}$ are hydrogen atoms or together form a group of the formula: —CH=CH—CH=CH—; R$^2$ and R$^3$ together form a group of the formula (a):

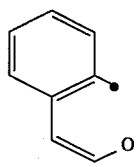

in which —● represent a bond to be bonded to the R$^3$ group, and —o represents a bond to be bonded to the R$^2$ group when R$^1$ and R$^{1'}$ together form a group of the formula: —CH=CH—CH=CH—, or when R$^1$ is a hydrogen atom, R$^2$ and R$^3$ together form a group of the formula: —CH=CH—CH=CH— or R$^2$ is a hydrogen atom and R$^3$ is an alkyl group which may be substituted by a halogen atom, a lower alkoxy group or a halogenated lower alkyl group, or a phenyl group which may be substituted by a halogen atom, a lower alkyl group or a halogenated lower alkyl group; A$^1$ is a 3-trifluoromethylphenyl group or a 3,5-bis(trifluoromethyl)phenyl group when R$^1$ is a hydrogen atom and R$^2$ and R$^3$ together form a group of the formula: —CH=CH—CH=CH—, or a phenyl group which may be substituted by a halogen atom, a lower alkyl group, a lower alkoxy group or a halogenated lower alkyl group when R$^1$ is not a hydrogen atom or when R$^2$ and R$^3$ do not together form a group of the formula: —CH=CH—CH=CH—.

2. The tertiary phosphine compound according to claim 1, which is an optically active substance.

3. A complex of a transition metal of Groups 8, 9 or 10 in the Periodic Table.. comprising a tertiary phosphine compound (1) as claimed in claim 1, as a ligand.

4. The complex of a transition metal according to claim 3, wherein said tertiary phosphine compound (1) is an optically active substance.

5. A process for producing an optically active organic silane compound of the formula (2):

(2)

wherein A$^2$ is a phenyl group which may be substituted by a halogen atom, a lower alkyl group, a lower alkoxy group or a halogenated lower alkyl group; R$^4$ is a hydrogen atom, a straight or branched alkyl group which may be substituted by an alkoxy group or a halogen atom or a cycloalkyl group which may be substituted by an alkoxy group or a halogen atom; and X, Y and Z are the same or different and represent a hydrogen atom, a halogen atom, an alkyl group or an alkoxy group comprising reacting a styrene derivative of the formula (3):

(3)

wherein A$^2$ and R$^4$ are the same as defined above, with a silane compound of the formula (4):

(4)

wherein X, Y and Z are the same as defined above, in the presence of a catalyst comprising a complex of a transition metal of Groups 8, 9 and 10 in the Periodic Table having an optically active substance of a tertiary phosphine compound (1) as claimed in claim 1 as a ligand.

* * * * *